(12) United States Patent
Keller et al.

(10) Patent No.: US 11,576,741 B2
(45) Date of Patent: Feb. 14, 2023

(54) MANIPULATOR SYSTEM WITH INPUT DEVICE FOR FORCE REDUCTION

(71) Applicant: KUKA Deutschland GmbH, Augsburg (DE)

(72) Inventors: Henrik Keller, Düsseldorf (DE); Salvatore Virga, Munich (DE)

(73) Assignee: KUKA Deutschland GmbH, Augsburg (DE)

( * ) Notice: Subject to any disclaimer, the term of this patent is extended or adjusted under 35 U.S.C. 154(b) by 609 days.

(21) Appl. No.: 16/617,602

(22) PCT Filed: May 22, 2018

(86) PCT No.: PCT/EP2018/063370
§ 371 (c)(1),
(2) Date: Nov. 27, 2019

(87) PCT Pub. No.: WO2018/219717
PCT Pub. Date: Dec. 6, 2018

(65) Prior Publication Data
US 2020/0179069 A1 Jun. 11, 2020

(30) Foreign Application Priority Data
May 30, 2017 (DE) .................... 10 2017 209 034.0

(51) Int. Cl.
*G05B 19/04* (2006.01)
*G05B 19/18* (2006.01)
(Continued)

(52) U.S. Cl.
CPC .............. *A61B 34/74* (2016.02); *A61B 34/30* (2016.02); *B25J 9/1633* (2013.01); *B25J 13/025* (2013.01); *B25J 13/085* (2013.01); *A61B 8/4218* (2013.01)

(58) Field of Classification Search
CPC ....... A61B 34/74; A61B 34/30; A61B 8/4218; A61B 8/429; A61B 8/4281;
(Continued)

(56) References Cited

U.S. PATENT DOCUMENTS 6,267,737 B1 7/2001 Meilus
6,585,668 B2 7/2003 Nissim
(Continued)

FOREIGN PATENT DOCUMENTS

AT 512834 B1 5/2014
DE 10108547 B4 4/2006
(Continued)

OTHER PUBLICATIONS

European Patent Office; Search Report in related International Patent Application No. PCT/EP2018/063370 dated Aug. 21, 2018; 3 pages.
(Continued)

*Primary Examiner* — Harry Y Oh
(74) *Attorney, Agent, or Firm* — Dorton & Willis, LLP

(57) ABSTRACT

A manipulator system includes a manipulator configured for guiding an instrument. The system furthermore includes a controller configured to actuate the manipulator such that the instrument is pressed with a pressing force against a human body. A force reduction input device is provided separately from the manipulator and is operable by an operator to reduce the pressing force.

14 Claims, 2 Drawing Sheets

(51) Int. Cl.
  *A61B 34/00* (2016.01)
  *A61B 34/30* (2016.01)
  *B25J 9/16* (2006.01)
  *B25J 13/02* (2006.01)
  *B25J 13/08* (2006.01)
  *A61B 8/00* (2006.01)

(58) Field of Classification Search
  CPC ......... A61B 2090/032; A61B 2090/065; B25J 9/1633; B25J 13/025; B25J 13/085; B25J 19/06; B25J 13/02
  See application file for complete search history.

(56) References Cited

U.S. PATENT DOCUMENTS

| | | |
|---|---|---|
| 10,456,919 B2 | 10/2019 | Schluesselberger, Sr. |
| 2004/0077939 A1 | 4/2004 | Graumann |
| 2007/0205785 A1 | 9/2007 | Nilsson |
| 2009/0088639 A1 | 4/2009 | Maschke |
| 2012/0022552 A1 | 1/2012 | Neff |
| 2014/0202961 A1* | 7/2014 | Marka ............. C02F 1/36 210/748.03 |
| 2017/0079871 A1 | 3/2017 | Zhang |
| 2017/0100838 A1* | 4/2017 | Lewis ............. B25J 9/1676 |
| 2018/0085926 A1 | 3/2018 | Kogan |

FOREIGN PATENT DOCUMENTS

| | | |
|---|---|---|
| DE | 102007046700 A1 | 4/2009 |
| DE | 102015204867 A1 | 9/2016 |
| DE | 202016106554 U1 | 12/2016 |
| DE | 102015222117 A1 | 5/2017 |
| EP | 2412406 A1 | 2/2012 |
| WO | 2017020081 A1 | 2/2017 |

OTHER PUBLICATIONS

European Patent Office; Written Opinion in related International Patent Application No. PCT/EP2018/063370 dated Aug. 21, 2018; 7 pages.

German Patent Office; Examination Report in related German Patent Application No. 10 2017 209 034.0 dated Feb. 28, 2018; 5 pages.

* cited by examiner

MANIPULATOR SYSTEM WITH INPUT DEVICE FOR FORCE REDUCTION

CROSS-REFERENCE TO RELATED APPLICATIONS

This application is a national phase application under 35 U.S.C. § 371 of International Patent Application No. PCT/EP2018/063370, filed May 22, 2018 (pending), which claims the benefit of priority to German Patent Application No. DE 10 2017 209 034.0, filed May 30, 2017, the disclosures of which are incorporated by reference herein in their entirety.

TECHNICAL FIELD

The present invention relates to a manipulator system as well as a method for controlling a manipulator.

BACKGROUND

Manipulators, and in particular robots, are freely programmable handling devices that can be used universally. A manipulator can have several axes that can be moved independently of each other by means of appropriate drives, such as servomotors. This allows the manipulator to adopt different poses or different configurations, for example to move an instrument to a certain position in space or to perform a certain process.

When used in medical technology, a manipulator can be used, for example, to perform a treatment, such as an examination or a procedure. For this purpose, the manipulator can guide the appropriate instrument or medical instrument, such as a scalpel or an ultrasound head. The manipulator can follow a trajectory or a path during the procedure or during the examination, or generally during the treatment, where the individual path points can be specified by a manipulator or robot program or a path planning.

In order to program a manipulator or robot program, the positions of individual path points, which are to be approached by the manipulator, must be recorded or specified. In so-called offline programming, for example, individual path points can be generated using appropriate models or simulation tools. In so-called online programming, programming takes place directly on the manipulator. This means that path planning can also be specified live, in which an operator controls the manipulator using an appropriate handling device.

When manipulators are used in medical technology, however, there is a major confidence problem. Many patients and even physicians do not trust a manipulator system to such an extent that they would use it unconditionally for a critical treatment step. For this reason, most manipulator systems in medical technology are configured merely as teleoperating or semi-autonomously. For example, a semi-autonomous manipulator can only be used as a support by holding an instrument orientation, while the operator or physician retains control over the contact between the instrument and the patient. For example, the orientation of a scalpel can be specified by the manipulator, while the forward movement is determined by the physician.

In surgical procedures, the patient is usually sedated, so that his confidence problem is not an issue during the procedure itself. However, in applications where the patient is not sedated and is in contact with the manipulator, the lack of confidence is a major problem. Such a situation can occur, for example, when an ultrasound probe is to be guided along the patient's body by a manipulator. In ultrasound examinations, an unpleasantly high pressure must often be applied to the patient with the ultrasound probe, as otherwise organs further inside the body are not clearly visible. If a doctor guides the ultrasound probe, the patient can talk to the physician if the pressure is too high and ask him to reduce the pressure. If a manipulator guides the ultrasound probe, however, such an intuitive possibility does not exist.

Another unpleasant situation may arise, if the ultrasound probe is pushed or pressed against the patient in a wrong or unfavorable orientation despite careful path planning, or if not enough ultrasound gel as a lubricant has been applied to the patient's skin, or if the ultrasound probe presses against a previously unknown (e.g. disease-related) sensitive area on the patient's body.

U.S. Pat. No. 6,267,737 B1 describes a robot system that can be used to repeatedly exert concentrated pressure on specific muscles in a patient's body. A maximum pressure can be set and when this pressure is exceeded, the robot is removed from the patient's body. The pressure is then mechanically released and the treatment is finally stopped.

SUMMARY

It is an object of the present invention to provide a manipulator system which overcomes the abovementioned problems, at least partially. In particular, it is an object of the present invention to enable an operator or patient to gain a certain degree of control over the manipulator in order to increase confidence.

These and other objects, which are apparent to the person skilled in the art from the following description, are solved by a manipulator system and method for controlling a manipulator as described herein.

The present invention relates to a manipulator system. The manipulator system comprises a manipulator, which can be configured as a multi-axis jointed-arm robot, for example. The manipulator is configured to guide an instrument. The instrument can, for example, form an end effector of the manipulator and can be the last element of a kinematic chain of the manipulator. The instrument can be an ultrasound probe, but also for example, a razor or other instrument for cosmetic applications. However, the invention is not limited to a specific instrument. In general, the instrument may be configured to perform a treatment, examination or procedure on a human body in direct contact with that body.

The manipulator system further comprises control means configured to control the manipulator in such a way that the instrument is pressed against the human body with a pressing force. The control means may be in the form of a controller, which may be implemented in the manipulator or provided separately from it. The human body, for example, can be a patient. Preferably, the instrument can be pressed against the human body according to a path planning. The path planning can be provided in advance, or can be the result of a manual, direct controlling of the manipulator by a user. The pressing force results from the contact between the instrument and the body. This pressing force can be, for example, one Newton. Depending on the application, the pressing force can also be well above or below one Newton. For example, the control means can be configured to control the manipulator in such a way that an ultrasound probe with such a pressing force is pressed against a patient so that an ultrasound examination can be performed.

The manipulator system further comprises a force reduction input means, which is provided separately from the manipulator. The force reduction input means can, for example, be configured as an input device, which is separate from the manipulator. The force reduction input means can communicate directly or indirectly with the control means, for example via a wireless or a wired interface. The force reduction input means can be operated by an operator in order to reduce the pressing force. The operator can be the person against whom the instrument is pressed (the human body), for example the patient, or a physician or another person who monitors the process.

The control means is further configured to control the manipulator such that the pressing force is reduced to an amount or value which is greater than zero based on a corresponding actuation of the force reduction input means. The pressing force is reduced, but the contact between the instrument and the human body is not cancelled, because the resulting pressing force remains greater than zero.

Using the force reduction input means, the operator can therefore reduce the force exerted by the manipulator. The controller can react to such a command from the operator and control the manipulator in such a way that the pressing force is reduced in a targeted manner without necessarily causing the treatment to be aborted. The use of the manipulator or the examination is not necessarily aborted, but can be continued with the reduced pressing force. Preferably, the pressing force is reduced while the path planning is being covered. The operator can thus carry out the force reduction interactively, i.e. directly during the examination. Advantageously, the treatment step can be continued with the reduced pressing force.

The person skilled in the art understands that the amount of pressing force exerted by the manipulator on the human body must not cause any serious injury to the body, depending on the type of application. Preferably, the pressing force can be in the range from 0.01 N to 100 N, further preferably in the range from 0.05 to 30 N, further preferably in the range from 0.1 N to 10 N.

Preferably, the force reduction input means is a user interface. The manipulator system is thus extended by such an interface for a patient, for example. Via this interface, the patient can always regulate the current pressure exerted by the manipulator system and can interactively reduce it. Preferably, the force reduction input means comprises a button, a switch, or a controller that can be operated manually. The operator can thus hold the force reduction input means in hand while lying on the treatment table, for example, and control the pressing force reduction directly by hand. If the manipulator exerts a force on the patient, the patient can intuitively reduce this force by pressing the button. Alternatively or additionally, other user interfaces can also be used, such as other button types, actuators, foot switches, voice interfaces, a brain-machine interface, face recognition, emotion recognition, eye tracking, patient pose tracking (e.g. using simple laser barriers), etc.

Preferably, the manipulator comprises force and/or torque sensors, which can register the forces or torques acting on the manipulator by means of strain gauges, for example. Alternatively, motor currents occurring in the drives of the manipulator can also be evaluated. Preferably, the control means is configured such that the manipulator can be controlled by means of force, position or hybrid control, the hybrid control designating a mixed form of force and position control. The reduction of the pressing force can preferably have a direct effect on this guide variable. In a pure position control, for example, the force can be reduced directly by controlling the position as the guide variable. By using force and/or torque sensors, the pressing force can be very efficiently determined directly and reduced according to the operator's input.

Preferably, the force reduction input means can also be operated by an operator to abort the pressing process. The force reduction input means thus comprises an additional function which allows an operator to abort the operation or the current treatment. For this purpose, the control means is preferably further configured to control the manipulator in such a way that the pressing force is reduced to zero and that the instrument is removed from the body or can be moved away manually (e.g. by switching the manipulator into a "soft" impedance mode (also called hand guidance mode) in which it can be pushed away by the patient), based on a corresponding actuation of the force reduction input means. A kind of "panic mode" can thus be activated by the operator's request to abort the pressing process. In this case, not only the pressing force is reduced, but the contact is broken off and the process is preferably aborted. Thus, in addition to the option of reducing the pressing force, the operator also has the option of aborting the process, if the necessary increase in confidence should not occur due to the reduction in pressing force.

Preferably, the force reduction input means can be operated analogously. For example, the force reduction input means can be operated continuously between two end positions. The force reduction input means can therefore preferably be configured as an analog controller. The control means is preferably set up to control the manipulator in such a way that the pressing force is reduced depending on the extent of the corresponding analog actuation of the force reduction input means. The reduction of the force can thus be dependent on the pressure depth of the analog controller. This allows the operator to precisely specify the extent to which the pressing force is to be reduced. In particular, the control means is preferably configured to control the manipulator in such a way that the pressing force is reduced proportionally or non-linearly to the extent of the corresponding analog actuation of the force reduction input means, or that the pressing force is reduced based on a time derivation of the extent of the corresponding analog actuation of the force reduction input means. The pressure depth is therefore preferably in direct relation to the resulting reduction in pressing force. In a preferred exemplary embodiment example, the extent of the force reduction can be influenced depending on the velocity or acceleration at which the analog actuation takes place.

Preferably, the force reduction input means can be digitally operated. The force reduction input means cannot be operated continuously, but discreetly. For example, a digital switch can be used to reduce the pressing force applied by the manipulator, or it can be switched directly to a "panic mode." The control means is preferably configured to control the manipulator in such a way that the pressing force is continuously reduced during a continuous corresponding digital actuation and/or in single steps during a repeated corresponding digital actuation and/or by a predefined factor or to a predefined amount during a single corresponding digital actuation. For example, if a digital button is used, the pressing force can be continuously reduced as long as the button remains pressed, and then the force applied when the button is released can be maintained. The digital button could also reduce the force in single steps by repeatedly pressing the button. By pressing the digital button once, the force could also be reduced by 50%, for example, and then slowly increased again until the button is pressed again, for example. Thus, very individual reaction strategies can be realized.

The force reduction input means is preferably configured to provide haptic feedback to the operator, preferably by means of vibration. For example, the operator or patient can be informed about the treatment or examination by means of vibration intensity or vibration intervals of a handle of the force reduction input means. For example, a vibration can be used to announce the beginning or end of an examination period.

Preferably, the control means is further configured to control the manipulator such that a movement of the instrument along the body is aborted and/or the instrument is removed from the body, when the manipulator system detects that the pressing force reduced to an amount or value greater than zero falls below a pressing force limit value. If, for example, the reduced pressing force is too low to achieve the desired examination or treatment result, the system could advantageously interrupt the application and generate a corresponding output to a physician, who supervises the examination or treatment. This person could then have a calming or informative effect on the patient or decide to switch to an alternative manual examination or treatment. Alternatively, the interruption could also be configured in such a way that, if the manipulator comprises force and/or torque sensors and is operated, for example, by means of impedance control (i.e. a special subform of force control), the manipulator holds the last pose and the pressing force continues to be controlled by the patient. If the patient permits an increased force again, by actuating the force reduction input means accordingly, the path planning can be continued. Alternatively, the examination or treatment could also be continued with the insufficient pressing force and, if necessary, a targeted second examination or treatment could be carried out at a later point in time. The position of an analog hand controller, which characterizes the pressing force limit value, could advantageously also be signaled haptically via the force reduction input means, for example by a noticeable resistance when exceeding this limit value.

Preferably, the manipulator system is configured to record measured values by means of the instrument during pressing. Preferably, the instrument can be configured for imaging and in particular for tomography. This allows the manipulator system to acquire corresponding image data.

Preferably, the manipulator system further comprises a measured value evaluation means, which is configured to record a quality of the measured values. For example, the quality of captured images can be determined with the help of a metric. Such a metric could be realized by Confidence Maps, ROI-Tracking or other techniques, with which the (complete) visibility of the respective anatomy can be determined. Preferably, the control means is also configured to control the manipulator based on the recorded quality of the measured values. For example, the pressing force can be reduced without input by the operator, if the quality of the measured values already allows it.

In particular, preferably the measurement evaluation means is further configured to determine whether the detected quality of the measured values falls below a quality limit. In particular, preferably the control means is further configured to control the manipulator in such a way that movement of the instrument along the body is interrupted and/or the instrument is removed from the body, if the measurement evaluation means determines that the detected quality of the measured values falls below the quality limit. Thus, if the reduced pressing force entails a correspondingly high loss of quality of the measured values, the treatment or examination can be paused or even aborted, for example, as described above.

Preferably, the manipulator system further comprises sensors for monitoring vital signs of the human body to determine a stress condition. For example, by measuring the pulse or the body temperature, it is possible to infer a patient's anxiety or stress condition. Furthermore, the manipulator system preferably comprises a stress evaluation means, which is configured to detect a stress condition of the body on the basis of the monitored vital signs and to determine whether the detected stress condition exceeds a stress limit value. Preferably, the control means is further configured to control the manipulator in such a way that the pressing force is reduced to zero and the instrument is removed from, or can be manually removed from the body, if the stress evaluation means determines that the detected stress condition exceeds the stress limit. Thus, the "panic mode" can be activated independently of the force reduction input means, if a corresponding panic condition of the patient is detected. This prevents the panic mode from being activated, even if the patient is unable to operate the force reduction input means, for example in a state of shock paralysis.

Preferably, the control means is further configured to control the manipulator such that the pressing force is continuously increased, and wherein the manipulator system is preferably configured to determine a maximum permissible pressing force based on an initial (while the pressing force is continuously increased) actuation of the force reduction input means. Thus, advantageously, the patient's personal sensation of pain can be recorded. Thus, in an initialization step that takes place before the actual examination, for example, the instrument can be pressed onto the patient's hand with constantly increasing pressing force, until the patient signals that his personal pain sensation has been reached by actuating the force reduction input means accordingly. The corresponding pressing force can be stored in the system as the maximum permissible pressing force and used for the following treatment steps.

By actuating the force reduction input means to reduce the pressing force, the pressing force or pressure is not necessarily cancelled mechanically. The application is therefore not necessarily terminated. Rather, the examination can be continued with reduced pressure or paused, if necessary. Preferably, no direct influence is exerted on the mechanics of the manipulator via the input means. Rather, the actuation is evaluated via the electronic manipulator control and then converted into a corresponding control.

The reduction of the pressing force can take place by means of a given mathematical function, which considers the duration of the actuation as input variable. As another or additional input variable, the amount of the pressure or pressing force currently generated by the manipulator can also be used, so that the reduction takes place faster with a very high pressing force than when the pressing force is already low.

The invention further relates to a procedure for controlling a manipulator, in which the manipulator guides an instrument. The process comprises pressing the instrument against a human body with a pressing force. This pressing can take place as part of the path planning process.

In a further step, it is detected during pressing whether an actuation at a force reduction input means is present, wherein the input means is provided separately from the manipulator and can be operated by an operator to reduce the pressing force.

Furthermore, if it is detected that a corresponding actuation of the force reduction input means is present, the manipulator is controlled in order to reduce the pressing force to an amount or value greater than zero.

The person skilled in the art understands that the components described above with regard to the manipulator system can also represent or describe corresponding steps in an inventive procedure. For example, the input means can be operable to abort the pressing force, and if it is detected that a corresponding actuation of the force reduction input means is present, the manipulator can be operated to reduce the pressing force to zero and to remove the instrument from the body. Furthermore, the pressing force can preferably be continuously increased in one initialization step until the input means is operated for the first time at a maximum permissible pressing force. Furthermore, the treatment can be aborted, if it is detected that the reduced pressing force falls below a pressing force limit value. Furthermore, measured values can be detected using the instrument, and if a detected quality of the measured values falls below a quality limit value, the treatment is aborted. Analogous to the description above, at least one vital sign of the human body can be monitored and, based on this, a stress condition of the body can be determined, and the pressing force can be reduced to zero and the instrument can be removed from the body, if it is detected that the determined stress condition exceeds the stress limit. This list of preferred procedural steps is not exhaustive, but complements the details described above with regard to the manipulator system for the person skilled in the art.

According to the invention, a manipulator system, such as the one described above, can be used to treat a patient, whereby the use can be at least partially as described above.

BRIEF DESCRIPTION OF THE DRAWINGS

The accompanying drawings, which are incorporated in and constitute a part of this specification, illustrate exemplary embodiments of the invention and, together with a general description of the invention given above, and the detailed description given below, serve to explain the principles of the invention.

DETAILED DESCRIPTION

Figure 1:
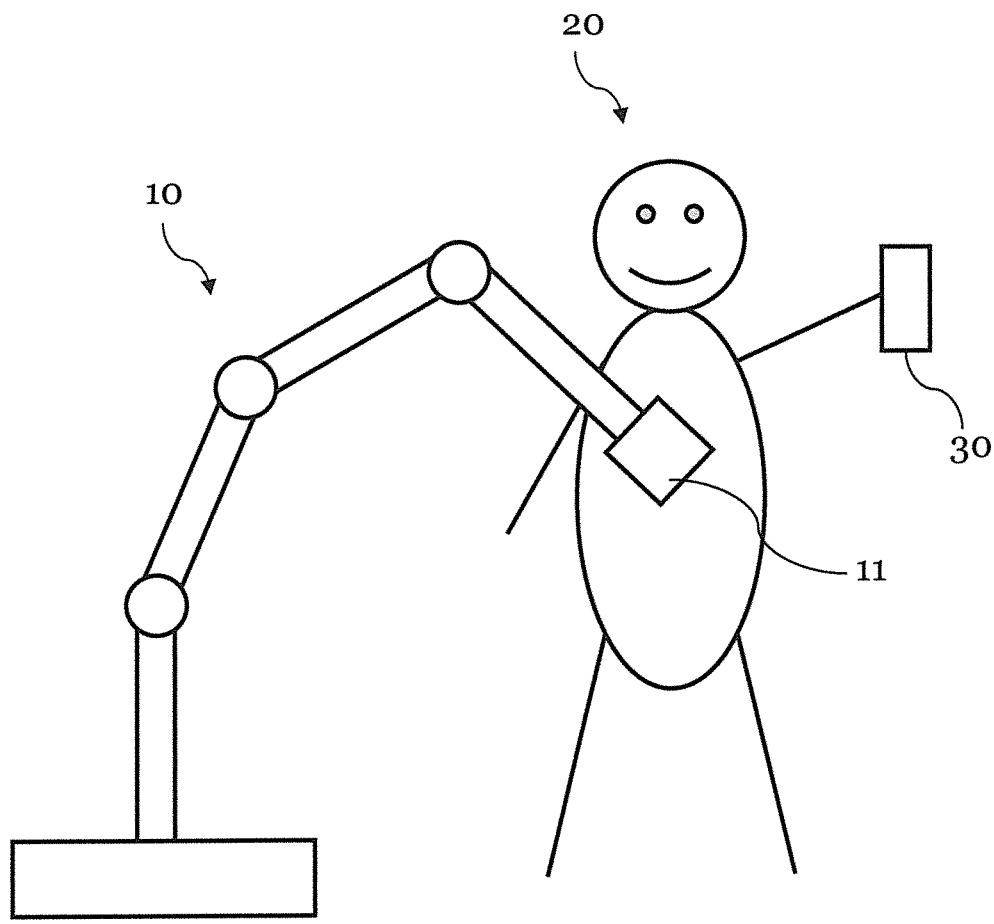
FIG. 1 shows a manipulator system according to an embodiment of the present invention.

FIG. 1 shows a manipulator system with which a treatment can be carried out on a human body or patient 20. A manipulator 10 is provided for this purpose, which is configured as a multi-axis jointed-arm robot. As end effector, the manipulator 10 comprises an instrument 11, which is configured as an ultrasonic probe 11, for example. The axes of the manipulator 10 are equipped with force-torque sensors, which make it possible to detect forces or torques that act on the manipulator 10. Thus, a pressing force can be detected, which is exerted on the body 20 by the manipulator 10. The manipulator 10 is operated by a hybrid control, which is a combination of impedance and position control.

The patient 20 holds a force reduction input means 30 in hand, which is configured in the form of a force reduction input device 30. It is wirelessly coupled to the manipulator 10, for example by means of radio or light wave technology. By operating the force reduction input device 30 accordingly, the patient 20 can reduce the pressing force exerted by the manipulator 10 on the patient 20 by means of the instrument 11.

Figure 2:
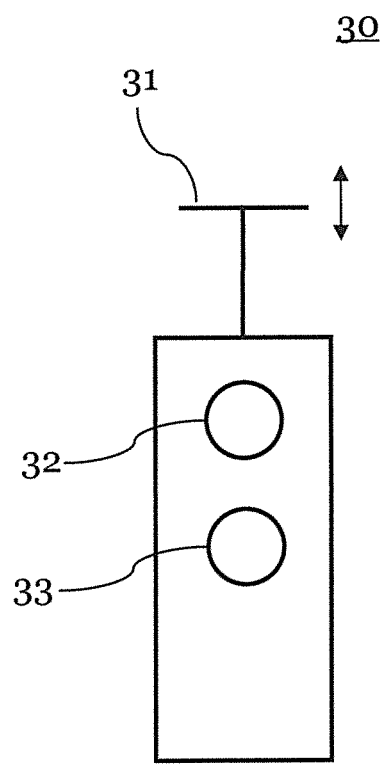
FIG. 2 shows a force reduction input means according to an embodiment of the present invention.

FIG. 2 shows an embodiment of the inventive force reduction input means 30, as used in the case of FIG. 1. The force reduction input means is configured as an input device 30 or as a hand-held device 30, which can be held in the hand by the patient 20 and operated by hand. The force reduction input device 30 comprises an analog controller 31 and two digital buttons 32, 33.

By pressing the analog controller 31 accordingly, the patient 20 can precisely specify how the force reduction is to take place. Depending on how far the analog controller 31 is pressed, the degree of reduction of the pressing force is controlled. The velocity of pressing the analog controller 31 can also be used to determine how fast or to what extent the force reduction is to take place. Advantageously, a "panic mode" can be initiated by pressing the analog controller 31 fully, in which the application is terminated and the manipulator 10 removes the instrument 11 from the patient 20. This position of the analog controller 31 can be characterized by an increased haptic resistance to prevent accidental switching to "panic mode." When the "panic mode" occurs, the pressing force can be reduced to zero and the manipulator 10 can slowly move away from the patient 20. Alternatively, the manipulator can also be switched to a "soft" impedance mode due to its force and torque sensors, so that it can easily be pushed away by the patient 20.

The "panic mode" can also be triggered by another button or sensor in the handle 30. For example, button 32 can be used as such a panic button. Button 32 can function similarly to an enabling switch, which must be pressed lightly to allow the manipulator 10 to perform its movement. If button 32 is pressed completely or not at all, this can be interpreted as a trigger for "panic mode."

Button 33 can be used as a digital switch as a user interface to set the pressure reduction. As button 33 is pressed, the pressing force is continuously reduced until button 33 is released. The "panic mode" can also be activated or triggered by pressing button 33 repeatedly and quickly.

The person skilled in the art understands that, according to the present invention, a force reduction input means can comprise one or a plurality of the controllers or buttons 31, 32, 33 described. At least a force reduction input means according to the present invention must make it possible to recognize an input of the operator, which specifies a pressing force reduction. Additional controls or buttons can be used for additional functions, such as triggering the "panic mode."

In the following, an exemplary embodiment of the present invention is described, whereby reference is made by way of example to the components of FIG. 1 and/or FIG. 2.

In this exemplary embodiment, the manipulator 10 is used to guide the ultrasound probe 11 over the abdomen of the patient 20, so that the aorta of the patient 20 can be examined. The forces that must be applied to the patient vary with the patient's anatomy. The person skilled in the art understands that forces above 20 N are not uncommon.

Before the actual examination, the system is put into a demonstration mode. The patient 20 holds the input device 30 in one hand, while the manipulator-guided ultrasound probe 11 is placed on the open palm of the other hand. The manipulator 10 now generates a force against the palm of the hand and the patient 20 can try out how to reduce this pressing force using the input device 30. This demonstration mode thus serves to create patient 20's confidence in the system.

The maximum permissible pressing force can now be measured in one initialization step: To do this, the manipulator 10 presses the ultrasound probe 11 against the palm of the hand again (or another place, such as preferably a place where the actual examination is to take place) of the patient 20, whereby the pressing force is constantly increased. As soon as the patient 20's personal pain threshold is reached, the patient actuates the input device 30. The current pressing force is stored in the system as the maximum permissible pressing force and the instrument 11 is removed again.

The patient 20 is then prepared and positioned for the examination, while still holding the input device 30 in hand. The manipulator 10 then performs the planned trajectory for the aorta examination using impedance control. The first steps here are usually a calibration step, where the manipulator 10 first determines the optimal orientation of the ultrasound probe 11 and the necessary force before carrying out the actual examination along the aorta's position. The patient 20 can reduce this optimal force at any time by actuating the input device 30. Depending on the actuation of the input device 30, the pressing force is reduced to a fixed or predefined minimum force.

Both for the demonstration mode and for the normal examination procedure, the impedance control of the manipulator 10 may be configured such that a force generated in the impact direction of the ultrasound probe 11 is multiplied by a factor generated according to the actuation of the input device 30 in order to reduce the pressing force. For example, a fully depressed controller 31 could correspond to a factor of 0.01, and a non-actuated controller 31 to a factor of 1. In all other directions and in orientation, the impedance control is set with high stiffness to prevent movements in these degrees of freedom. When using a hybrid control, these degrees of stiffness could then also be position-controlled.

Preferably, a measurement of the pressing force performed with the manipulator 10 can also be considered to reduce this pressing force. This is made possible by the force-torque sensor technology of the manipulator 10. Preferably, the force reduction is only caused by a movement of the manipulator arm, so that collisions of the manipulator 10 with its surroundings are prevented.

Since the manipulator 10 is equipped with force-torque sensors, a deviation from expected application-typical forces can preferably be detected and the described "panic mode" can also be triggered here when a permitted tolerance threshold is exceeded. Such deviations could, for example, affect the force direction, force level or the point of application of a force. Thus, it can be detected that the patient 20 tries to push the manipulator 10 away. The patient 20, for example, could be so insecure that he does not pay attention to the input device 30, but instinctively tries to push the manipulator 10 away.

Although the present description describes that the patient operates the input device, an attendant or physician can also hold the input device in hand and reduce the force by consulting the patient. However, the best effect on confidence-building in the system is achieved when the patient himself specifies the reduction of the pressing force.

While the present invention has been illustrated by a description of various embodiments, and while these embodiments have been described in considerable detail, it is not intended to restrict or in any way limit the scope of the appended claims to such detail. The various features shown and described herein may be used alone or in any combination. Additional advantages and modifications will readily appear to those skilled in the art. The invention in its broader aspects is therefore not limited to the specific details, representative apparatus and method, and illustrative example shown and described. Accordingly, departures may be made from such details without departing from the spirit and scope of the general inventive concept.

What is claimed is:

1. A manipulator system, comprising:
   a robotic manipulator configured for guiding an instrument;
   a controller configured to actuate the robotic manipulator such that the instrument is pressed with a pressing force against a human body; and
   a force reduction input device separate from the manipulator and operable by an operator to reduce the pressing force;
   wherein the controller is further configured to control the manipulator such that the pressing force is reduced to an amount greater than zero based on a corresponding actuation of the force reduction input device; and
   wherein the controller is further configured such that, in response to a determination by the manipulator system that the magnitude of the pressing force has been reduced below a pressing force limit value that is greater than zero, the controller controls the robotic manipulator to at least one of:
   abort a movement of the instrument along the body, or
   remove the instrument from the body.

2. The manipulator system of claim 1, wherein the force reduction input device is a user interface comprising a button, switch, or a variably adjustable control input structure, which can preferably be operated by hand.

3. The manipulator system of claim 1, wherein:
   the robotic manipulator comprises at least one of force or torque sensors; and
   the controller is configured to control the robotic manipulator by force control, position control, or hybrid control.

4. The manipulator system of claim 1, wherein:
   the force reduction input device is further operable by an operator to abort the pressing; and
   the controller is further configured to control the robotic manipulator such that the pressing force is reduced to zero and the instrument is removed from, or can be manually removed from, the body based on a corresponding actuation of the force reduction input device to abort the pressing.

5. The manipulator system of claim 1, wherein:
   the force reduction input device is configured to receive a variable tactile analog input applied by the operator; and
   the controller is configured to control the robotic manipulator such that the pressing force is reduced depending on an extent of the corresponding analog actuation of the force reduction input device.

6. The manipulator system of claim 5, wherein the controller is configured to control the robotic manipulator such that the pressing force is reduced proportionally or non-linearly based on the extent of the corresponding analog actuation of the force reduction input device, or based on a time derivation of the extent of the corresponding analog actuation of the force reduction input device.

7. The manipulator system of claim 1, wherein:
   the force reduction input device is digitally operable; and the controller is configured to control the robotic manipulator such that at least one of:
the pressing force is continuously reduced during a sustained corresponding digital actuation,
the pressing force is reduced in single steps during a repeated corresponding digital actuation, or
the pressing force is reduced by a predefined factor or to a predefined value during a single corresponding digital actuation.

8. The manipulator system of claim 1, wherein the force reduction input device is configured to output a haptic feedback to the operator.

9. The manipulator system of claim 8, wherein the haptic feedback comprises vibration.

10. The manipulator system of claim 1, further comprising:
a plurality of sensors configured to monitor vital signs of the body for determining a stress condition; and
a stress evaluation means configured to determine a stress condition of the body based on the monitored vital signs, and to determine whether the detected stress condition exceeds a stress limit;
wherein the controller is further configured to control the robotic manipulator such that the pressing force is reduced to zero and the instrument is removed from the body, or can be manually removed from the body, when the stress evaluation means determines that the detected stress condition exceeds the stress limit.

11. The manipulator system of claim 1, wherein:
the controller is further configured to control the robotic manipulator such that the pressing force is continuously increased; and
the manipulator system is configured to determine a maximum permissible pressing force based on a first actuation of the force reduction input device while continuously increasing the pressing force.

12. A method of controlling a robotic manipulator, wherein the robotic manipulator is configured to guide an instrument, the method comprising:
controlling the robotic manipulator to press the instrument against a human body with a pressing force;
during pressing, detecting whether an actuation is present at a force reduction input device, wherein the force reduction input device is separate from the robotic manipulator and is operable by a user to reduce the pressing force;
controlling the robotic manipulator to reduce the pressing force to an amount greater than zero in response to detecting actuation of the force reduction input device; and
in response to a determination that the magnitude of the pressing force has been reduced below a pressing force limit value that is greater than zero, controlling the robotic manipulator to at least one of:
abort a movement of the instrument along the body, or
remove the instrument from the body.

13. The method of claim 12, wherein the instrument is configured for imaging.

14. The manipulator system of claim 1, wherein the instrument is configured for imaging.

* * * * *